United States Patent
Murphy et al.

(10) Patent No.: US 9,937,038 B2
(45) Date of Patent: Apr. 10, 2018

(54) CRIMPING TOOL FOR A PROSTHETIC DEVICE AND METHOD FOR CRIMPING A PROSTHETIC DEVICE WITH A CRIMPING TOOL

(71) Applicant: BIOTRONIK AG, Buelach (CH)

(72) Inventors: Brian Murphy, Galway (IE); Markus Hepke, Zurich (CH); Nils Le Cerf, Zollikon (CH)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 14/434,020

(22) PCT Filed: Jul. 31, 2013

(86) PCT No.: PCT/EP2013/066057
§ 371 (c)(1),
(2) Date: Apr. 7, 2015

(87) PCT Pub. No.: WO2014/056644
PCT Pub. Date: Apr. 17, 2014

(65) Prior Publication Data
US 2015/0250587 A1 Sep. 10, 2015

Related U.S. Application Data

(60) Provisional application No. 61/711,230, filed on Oct. 9, 2012.

(51) Int. Cl.
*A61F 2/95* (2013.01)
*A61F 2/24* (2006.01)

(52) U.S. Cl.
CPC .......... *A61F 2/2427* (2013.01); *A61F 2/2436* (2013.01); *A61F 2/95* (2013.01);
(Continued)

(58) Field of Classification Search
CPC ................ A61F 2/95; A61F 2002/9522; A61F 2240/001; Y10T 29/53657;
(Continued)

(56) References Cited

U.S. PATENT DOCUMENTS

| 4,107,964 A | * | 8/1978 | Smith | .................. B21D 39/046 |
| | | | | 29/237 |
| 4,215,871 A | * | 8/1980 | Hirsch | ................ B23B 31/1253 |
| | | | | 279/46.3 |

(Continued)

FOREIGN PATENT DOCUMENTS

| EP | 0903122 | 3/1999 |
| WO | 2003/079933 A1 | 10/2003 |

OTHER PUBLICATIONS

PCT/EP2013/066057 International Search Report dated Oct. 24, 2013.

*Primary Examiner* — Jermie Cozart
(74) *Attorney, Agent, or Firm* — Wagenknecht IP Law Group PC

(57) ABSTRACT

A crimping tool and method for reducing an external dimension of a compressible prosthetic device, the crimping tool comprising a first member comprising a first control surface collapsible between a first state and a second state, the first member having a first open end configured for introducing the prosthetic device when the first control surface is in the first state, and a second open end configured for allowing locking of the prosthetic device when introduced into the first member; an engagement portion that moves the first control surface from the first state to the second state; and an actuator portion for moving the first member along the longitudinal axis allowing the engagement portion to interact with the first member.

5 Claims, 11 Drawing Sheets

(52) U.S. Cl.
CPC . *A61F 2002/9522* (2013.01); *A61F 2240/001* (2013.01); *Y10T 29/49913* (2015.01); *Y10T 29/49934* (2015.01); *Y10T 29/53987* (2015.01)

(58) Field of Classification Search
CPC ......... Y10T 29/53678; Y10T 29/53987; Y10T 29/49913; Y10T 29/49927; Y10T 29/49929; Y10T 29/49934; Y10T 29/53687; Y10T 29/53909
USPC .......................................................... 623/1.11
See application file for complete search history.

(56) References Cited

U.S. PATENT DOCUMENTS

| | | | |
|---|---|---|---|
| 5,626,604 A | 5/1997 | Cottone, Jr. | |
| 5,749,921 A * | 5/1998 | Lenker | A61F 2/95 606/194 |
| 5,810,873 A * | 9/1998 | Morales | A61F 2/958 606/1 |
| 5,992,000 A * | 11/1999 | Humphrey | A61F 2/958 29/282 |
| 6,068,635 A * | 5/2000 | Gianotti | A61F 2/95 29/235 |
| 6,167,605 B1 * | 1/2001 | Morales | A61F 2/958 29/282 |
| 6,702,845 B1 * | 3/2004 | Cully | A61F 2/95 29/282 |
| 6,981,982 B2 * | 1/2006 | Armstrong | A61F 2/07 29/282 |
| 7,691,109 B2 * | 4/2010 | Armstrong | A61F 2/07 606/108 |
| 8,359,721 B2 * | 1/2013 | Melsheimer | A61F 2/95 29/235 |
| 8,468,667 B2 * | 6/2013 | Straubinger | A61F 2/2427 29/237 |
| 9,021,670 B2 * | 5/2015 | Dale | A61F 2/2427 29/235 |
| 9,056,001 B2 * | 6/2015 | Armstrong | A61F 2/07 |
| 9,168,135 B2 * | 10/2015 | Dale | A61F 2/2427 |
| 9,308,346 B2 * | 4/2016 | Soundararajan | A61F 2/95 |
| 2002/0035390 A1 | 3/2002 | Schaldach et al. | |
| 2010/0057185 A1 | 3/2010 | Melsheimer et al. | |
| 2012/0083874 A1 * | 4/2012 | Dale | A61F 2/2427 623/2.11 |
| 2014/0215791 A1 * | 8/2014 | Soundararajan | A61F 2/95 29/428 |
| 2014/0277364 A1 * | 9/2014 | Sarac | A61F 2/97 623/1.12 |
| 2014/0331475 A1 * | 11/2014 | Duffy | A61F 2/243 29/446 |
| 2015/0135647 A1 * | 5/2015 | Dale | A61F 2/2427 53/436 |

* cited by examiner

CRIMPING TOOL FOR A PROSTHETIC DEVICE AND METHOD FOR CRIMPING A PROSTHETIC DEVICE WITH A CRIMPING TOOL

CROSS REFERENCE TO RELATED APPLICATIONS

This is a Section 371 US national phase entry of PCT/EP2013/066057, filed Jul. 31, 2013, which claims benefit of priority to U.S. provisional patent application Ser. No. 61/711,230 filed Oct. 9, 2012; the contents of each are herein incorporated by reference in their entirety.

TECHNICAL FIELD

Summary of the Invention

The invention relates a crimping tool for a prosthetic device and a method for crimping a prosthetic device with a crimping tool.

BACKGROUND OF THE INVENTION

There are several tools known in the art for crimping a prosthetic device such as a stent or a prosthetic heart valve or the like to a small diameter so that the prosthetic device can be introduced into a human or animal body minimally invasive via a catheter.

U.S. Pat. No. 5,911,752 discloses to collapse a stent by deforming a portion of the stent beyond the elastic limit. The stent is pushed through a frustoconical body which causes collapsing of the stent thus reducing its outer diameter.

WO 2010/096176 A1 discloses a crimping tool for a collapsible prosthetic device such as a prosthetic heart valve, said tool having a plurality of resilient tines defining an array around a longitudinal axis of the crimping tool. The plurality of tines is adapted to intersect a plurality of openings in the prosthetic device in an assembled position of the crimping tool on the prosthetic device to prevent pinching of the prosthetic device structure by its stent frame as the prosthetic device is collapsed. Subsequently, the prosthetic device with the tines is pushed through a frustoconical body for collapsing the prosthetic device.

WO 2007/120543 discloses a crimping tool having a first reducing member comprising a first tapered surface and a second reducing member comprising a second tapered surface. The prosthetic device is collapsed by moving the prosthetic device along a tapered surface of the first member and drawn into a sheath of a catheter.

It is an object of the invention to provide a crimping tool with improved handling and which allows for a gentle processing of a collapsible prosthetic device.

Another object is to provide a method for a method for crimping a prosthetic device with a crimping tool.

The objects are achieved by the features of the independent claims. The other claims, the description and the drawings provide advantageous developments of the invention.

In a first aspect of the invention a crimping tool for reducing an external dimension of a compressible prosthetic device is proposed, said crimp tool comprising a first member having a longitudinal axis and comprising a first control surface, said first control surface being collapsible between a first state and a second state, said first member having a first open end and a second open end, the first open end being configured for introducing the prosthetic device when the first control surface is in said first state, and said second open end being configured for allowing locking of the prosthetic device, when introduced into the first member, to the first member;

an engagement portion for causing the first control surface to at least move from the first state to the second state when interacting with the first member; and an actuator portion for moving the first member along the longitudinal axis for allowing the engagement portion to interact with the first member.

It is of advantage that the prosthetic device can easily be locked to the first member when it protrudes from the second open end of the first member, e.g. by usage of a splint or the like. As a result, the inserted prosthetic device moves with the first member when the first member is moved, e.g. pulled through the engagement portion along the longitudinal axis. When the prosthetic device comes into contact with the first control surface, the collapsible prosthetic device can collapse in conjunction with the first control surface. As it is the outer surface of the first member which experiences a sliding movement relative to the engagement portion, the outer surface of the prosthetic device is protected from damage caused by sliding movements.

Advantageously, the crimping tool is easy to handle even in a saline bath in a sterile environment of an operating theatre which is required for handling of e.g. a prosthetic heart valve or the like. The overall dimensions of the crimping tool are reasonable so that an overlarge saline bath is not necessary. There are only few parts and steps necessary for collapsing the prosthetic device. Manipulating the crimping tool is easy to teach and to learn. Handling of the crimping tool is intuitive and systematic. The crimping tool is low weight and economically priced. Because there are not so many parts necessary, the danger of an individual part being dropped on the floor is reduced.

In an advantageous embodiment, the first member may be slidably arranged in a second member having a first open end and an opposing second open end. The second member allows for a stable arrangement and secure movement of the first member, thus allowing for a controlled collapsing of the prosthetic device.

In an advantageous embodiment, the second end may comprise the engagement portion, said engagement portion having an opening for allowing a sliding movement of the first member along the longitudinal axis. The arrangement is particularly compact and stable. In particular, the engagement portion may be a ring being arranged at the second end of the second member. When the prosthetic device is arranged in the first member, the prosthetic device collapses when the first member collapses.

In an advantageous embodiment, the first member may be configured as a collet having a receiving sleeve comprising a multitude of shell portions separated by cuts predominantly parallel to the longitudinal axis, said multitude of shell portions forming a splayed shell in the first state of the first member, said multitude of shell portions being attached to a ring.

For instance, the first member can be imagined as a piece of bamboo split with a knife into several, e.g. six, pieces on one end. These several pieces are splayed out to create a cone shape. The prosthetic device may be inserted into this cone, when the cone is collapsed to its original shape the prosthesis is crimped.

In an advantageous embodiment, the second member may be a cage structure configured to enclose the first member when said first member is in said first state. This allows for a low weight and stable arrangement.

In an advantageous embodiment, a third member is provided which is releasably connectable to the first end of the first member. The third member may provide additional and mild support for the prosthetic device when introduced into the first member. The third member may be in form of a cap which closes the first open end of the first member.

In an advantageous embodiment, the third member may comprise a screw thread for connecting to the first member. Thus, the third member can be easily connected, i.e. screwed, to the first member, while the prosthetic device is pushed into the first member. In alternative embodiments, a connection between the third member can be established via a bayonet lock, a friction lock or the like.

In an advantageous embodiment, the third member may have a receptacle for a portion of the prosthetic device. The prosthetic device can be arranged with one end in the third member and with an opposite end be pushed into the first member while the third member is attached to the first member.

In an advantageous embodiment, the receptacle may be an annular collar arranged on the third member. This allows for a simple mounting of the prosthetic device.

In another aspect of the invention a method for crimping a prosthetic device with a crimp tool is proposed by performing the steps
   providing a first member having a longitudinal axis and comprising a first control surface, said first control surface being collapsible between a first state and a second state, said first member having a first open end and a second open end, the first open end being configured for introducing the prosthetic device when the first control surface is in said first state, and said second open end being configured for allowing locking of the prosthetic device, when introduced into the first member, to the first member;
   providing an engagement portion for causing the first control surface to at least move from the first state to the second state when interacting with the first member;
   providing an actuator portion for moving the first member along the longitudinal axis for allowing the engagement portion to interact with the first member; and
   collapsing the first control surface from the first state to the second state by passing the first member through the engagement portion in direction of the longitudinal axis.

Advantageously, the method is a gentle of crimping with reduced trauma to external stitches of the prosthetic device, e.g. a prosthetic heart valve or the like.

Particularly, the prosthetic device may be pushed and locked into a first member such as a cone until capture tangs of the prosthetic device protrude. The tangs may be locked onto a catheter. Then a collet may be moved forward by holding the hooks in place and pulling the lock ring forward. This action collapses the conical first body to a cylinder and crimps the prosthetic device. The prosthetic device can now be loaded to a loading area of a catheter.

In an advantageous embodiment, a second member may be provided including the engagement portion for interacting with the first member, thus facilitating the movement of the first member.

In an advantageous embodiment, a third member may be provided for introducing the prosthetic device into the first member. The third member can be utilized for pushing the prosthetic device into the first member.

The present invention together with the above-mentioned and other objects and advantages may best be understood from the following detailed description of the embodiments, but not restricted to the embodiments, wherein is shown in:

DETAILED DESCRIPTION OF PREFERRED EMBODIMENTS

Figure 1:
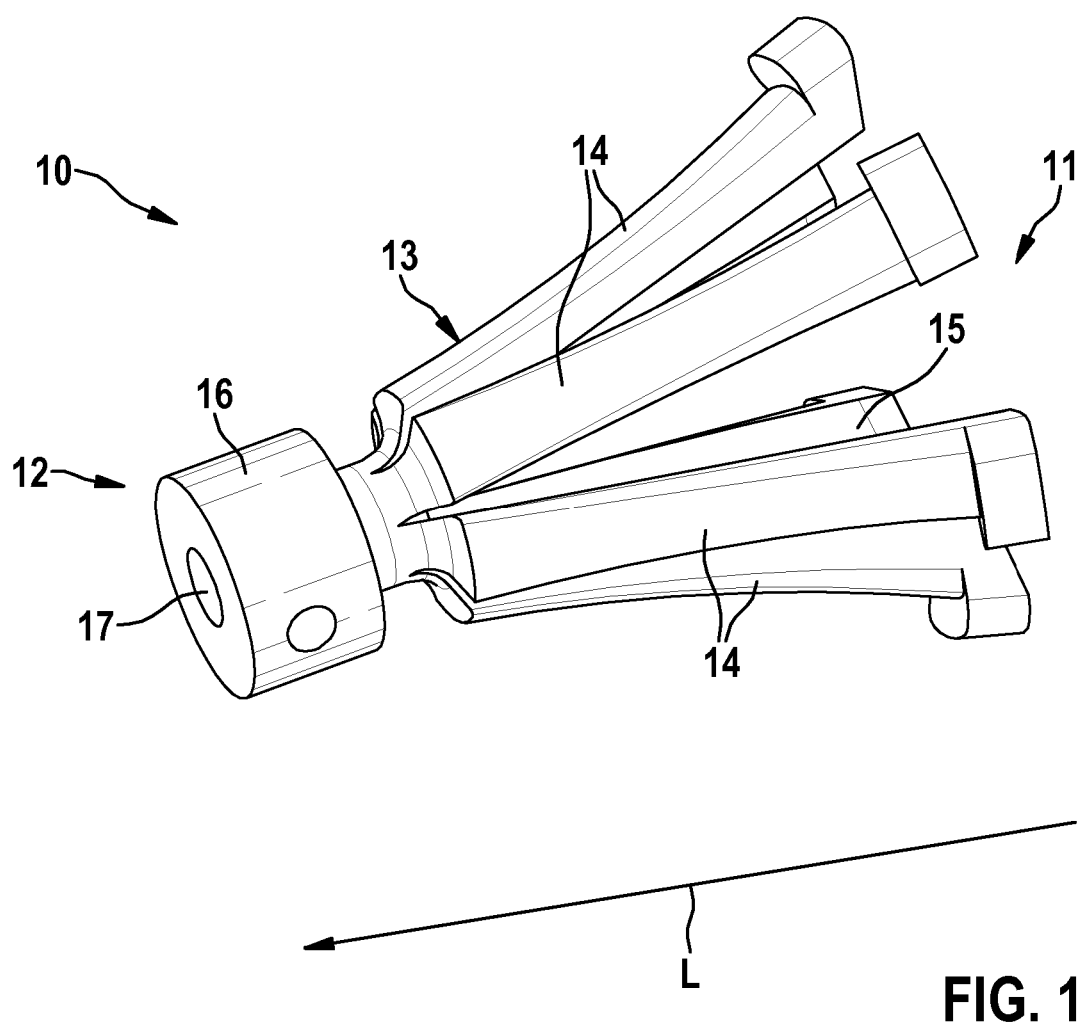
FIG. 1 a perspective view of an embodiment of a first member of a prosthetic crimp tool according to the invention.

In the drawings, like elements are referred to with equal reference numerals. The drawings are merely schematic representations, not intended to portray specific parameters of the invention. Moreover, the drawings are intended to depict only typical embodiments of the invention and therefore should not be considered as limiting the scope of the invention.

Figure 2:
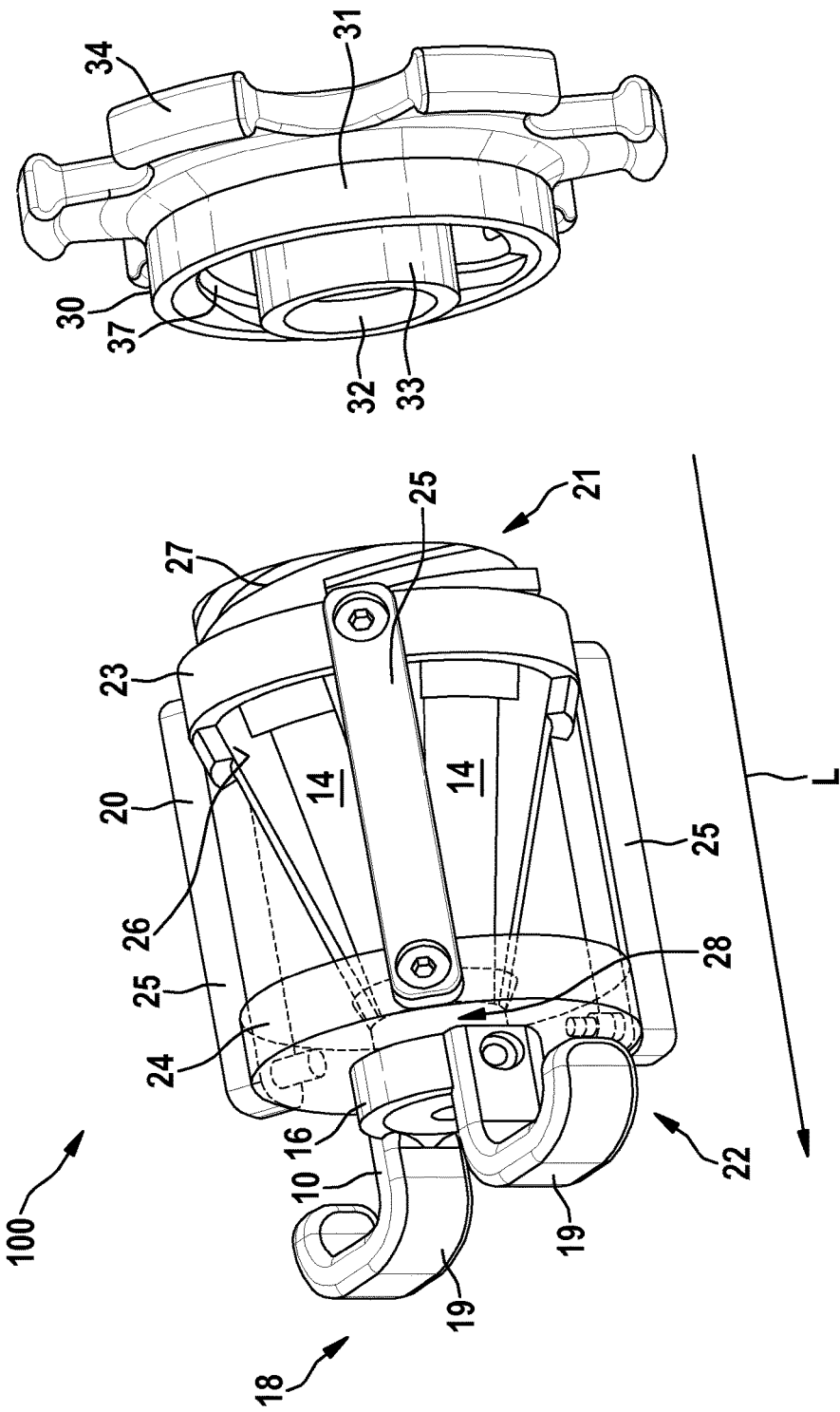
FIG. 2 a perspective view of an embodiment of a prosthetic crimp tool having first, second and third members.
Figure 3:
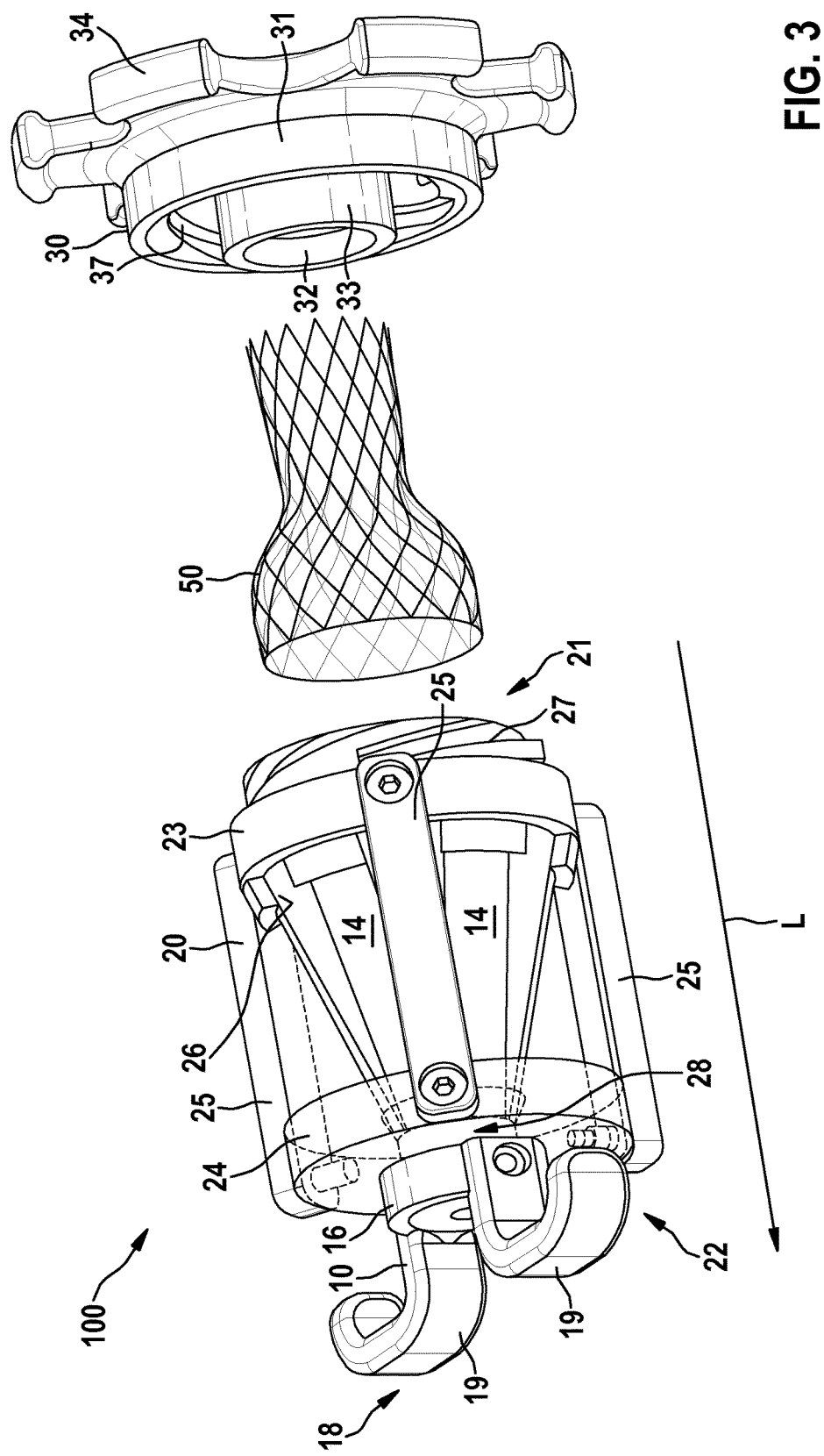
FIG. 3 an exploded view of an embodiment of a prosthetic crimp tool depicting a collapsible prosthetic device to be crimped with the prosthetic crimp tool.

FIGS. 1 and 2 illustrate components of an embodiment of a prosthetic crimping tool 100. FIG. 3 shows in an exploded view the components of the crimping tool 100 and a collapsible prosthetic device 50 which is to be crimped with the crimping tool 100. FIG. 1 depicts in a perspective view an embodiment of a first member 10 for the prosthetic crimping tool 100 depicted in FIG. 2. The crimping tool 100 is utilized for reducing an external dimension of the compressible prosthetic device 50. In this embodiment, the crimp tool 100 comprises the first member 10, a second member 20 and a third member 30, as shown in FIG. 2.

The components of the crimping tool 100, particularly the first and second members 10, 20 have a longitudinal axis L.

The prosthetic device 50 such as a stent, a prosthetic heart valve or the like, is introduced in the crimping tool 100 predominantly parallel to the longitudinal axis L.

The first member 10 comprises a first control surface 15, said first control surface 15 being collapsible between a first state, e.g. a state with frustoconical form of a shell 13 of the first member 10 and a second state, e.g. a state with a cylindrical form of the shell 13. The interior surface of the first member 10 forms the first control surface 15.

The first member 10 has a first open end 11 and an opposing second open end 12. The first open end 11 is configured for introducing the prosthetic device 50 when the first control surface 15 is in said first state, and said second open end 12 is configured for allowing locking of the prosthetic device 50, when introduced into the first member 10, to the first member 10. When the prosthetic device 50 is fully introduced in the crimping tool 100, securing tangs can protrude through an opening 17 of the second open end 12 where the tangs and, consequently, the prosthetic device, can be locked in place relative to the first member 10.

The second member 20 has a first open end 21 and an opposing second open end 22 where an engagement portion 24 for causing the first control surface 15 to at least move from the first state to the second state when interacting with the first member 10 is arranged at the second open end. The engagement portion 24 has an annular shape with a central opening 28 through which the prosthetic device 50 can protrude.

The first member 10 is slidably arranged in the second member 20. The first member 10 can be moved along the longitudinal axis L through the opening 28, having a smaller diameter than the first open end 11 in the first state of the first member 10.

The first member 10 is configured as a collet having a receiving sleeve comprising a multitude of shell portions 14 separated by cuts predominantly parallel to the longitudinal axis L, said multitude of shell portions 14 forming a splayed shell 13 in the first state of the first member 10, said multitude of shell portions 14 being attached to a ring 16 at the second open end 12. The first member 10 can be imagined as a piece of bamboo split with a knife into several, e.g. six, pieces on the first open end 11. These several pieces (shell portions 14) are splayed out to create a cone shaped shell 13. The prosthetic device 50 may be inserted into this cone. When the cone is collapsed to its original shape the prosthetic device 50 is crimped.

The second member 20 is a cage structure configured to enclose the largest portion of the first member 10 when said first member 10 is in said first state. At a first open end 21 a ring 23 with a large opening is arranged and spaced from the annular engagement portion 24 having an opening 28 with a smaller diameter at the opposing open end 22 by longitudinal bars 25. The cage structure has a cylindrical cross section.

The second member 20 comprises shell portions 25 in its inner volume forming a frustoconical shell which shell portions 25 cooperate with the shell portions 14 of the first member 10 in the first state to form a closed conical shell.

The first member 10 has an actuator portion 18 with two hooks 19 for moving the first member 10 along the longitudinal axis L through the opening 28 for allowing the engagement portion 24 to interact with the first member 10. The fingers of an operator can engage the hooks 19 so that the operator can comfortably pull the first member 10 along the longitudinal axis L.

The crimping tool 100 has a third member 30 which is releasably connectable to the first end 21 of the second member 20, e.g. by screwing it with a screw thread 37 to a thread 27 at the first end 21 of the second member 20. The third member 30 is a cap which closes the first open ends 11, 21 of the first and second member 10, 20. The third member 30 has an annular receptacle 32 for an end portion of the prosthetic device 50 which can be inserted into the annulus 33 of the receptacle 32. The thread 37 is arranged as an internal thread on a ring 31. At its outer diameter, the third member 30 provides a plurality of radially pointing pegs 34 which facilitates screwing the third member 30 to the second member 20.

Figure 4:
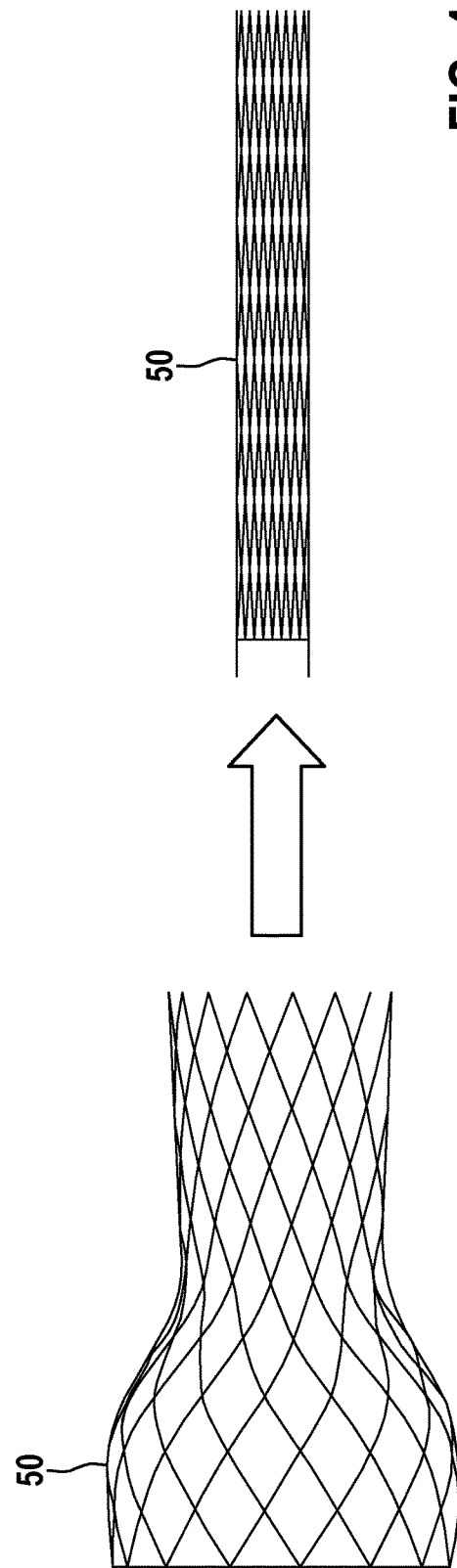
FIG. 4 a side view of a collapsible prosthetic device in a non-collapsed and a collapsed state.

FIG. 4 exemplifies a collapsible prosthetic device 50 pre and after the crimping process with the crimping tool 100.

Figure 5:
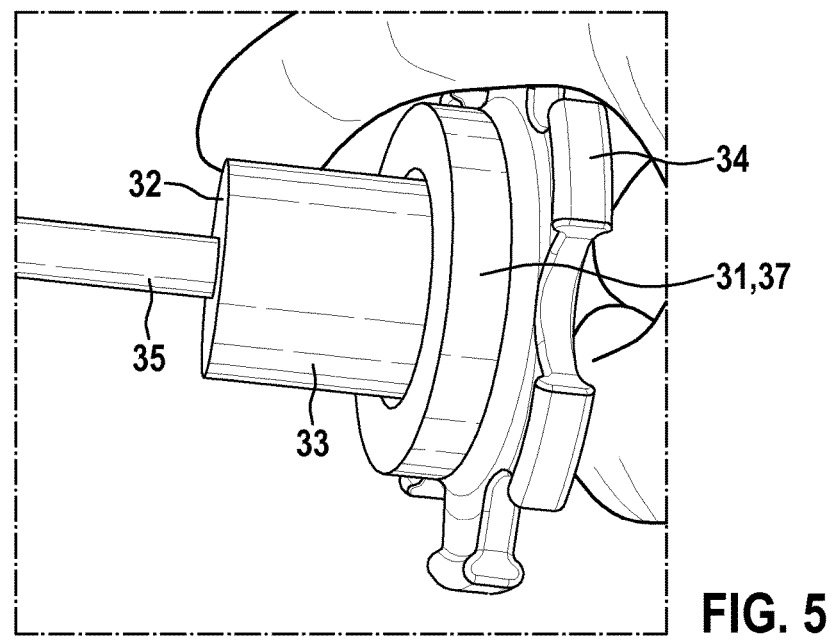
FIG. 5 a side view of another embodiment of a third member having a rod-like centre piece for orienting and stabilizing a collapsible prosthetic device.

FIG. 5 shows in a side view another embodiment of a third member 30 having a rod-like centre piece 35 for orienting and stabilizing a collapsible prosthetic device in a receptacle 32. The prosthetic device 50 is arranged about the centre piece 35. The centre piece 35 is particularly useful for introducing a catheter tip portion into the crimping tool 100. Whereas the prosthetic device 50 (FIG. 3) is introduced through the first ends 11, 21 of the first and second members 10, 20, such a catheter tip portion is inserted in the crimping tool 100 from the opposite side.

Figure 6:
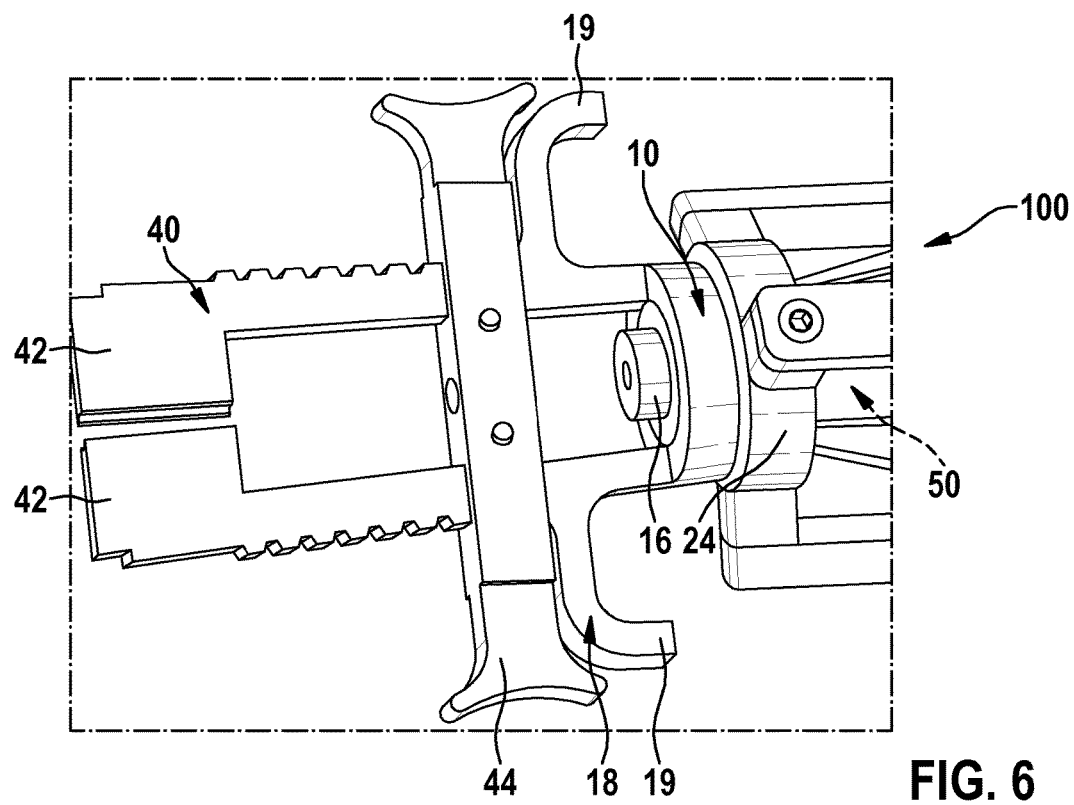
FIG. 6 an embodiment of a crimping tool having a mechanism for introducing and releasing a catheter tip portion.

FIG. 6 illustrates a detail of an embodiment of a crimping tool 100 having a mechanism for introducing and releasing a catheter tip portion. A gripper element 40 with two legs 42 is attached to an actuator portion 18 depicted with two hooks 19 of the first member 10. The two legs 42 can be pressed together or released with a slider 44.

In FIGS. 7a to 7f several method steps in a saline bath are shown where the crimping tool 100 is used to crimp and mount a collapsible prosthetic device (not to be seen in the drawing) to a catheter tip portion 60. The crimping tool 100 is predominantly configured as described before but has an additional gripper element 40.

Figure 7A:
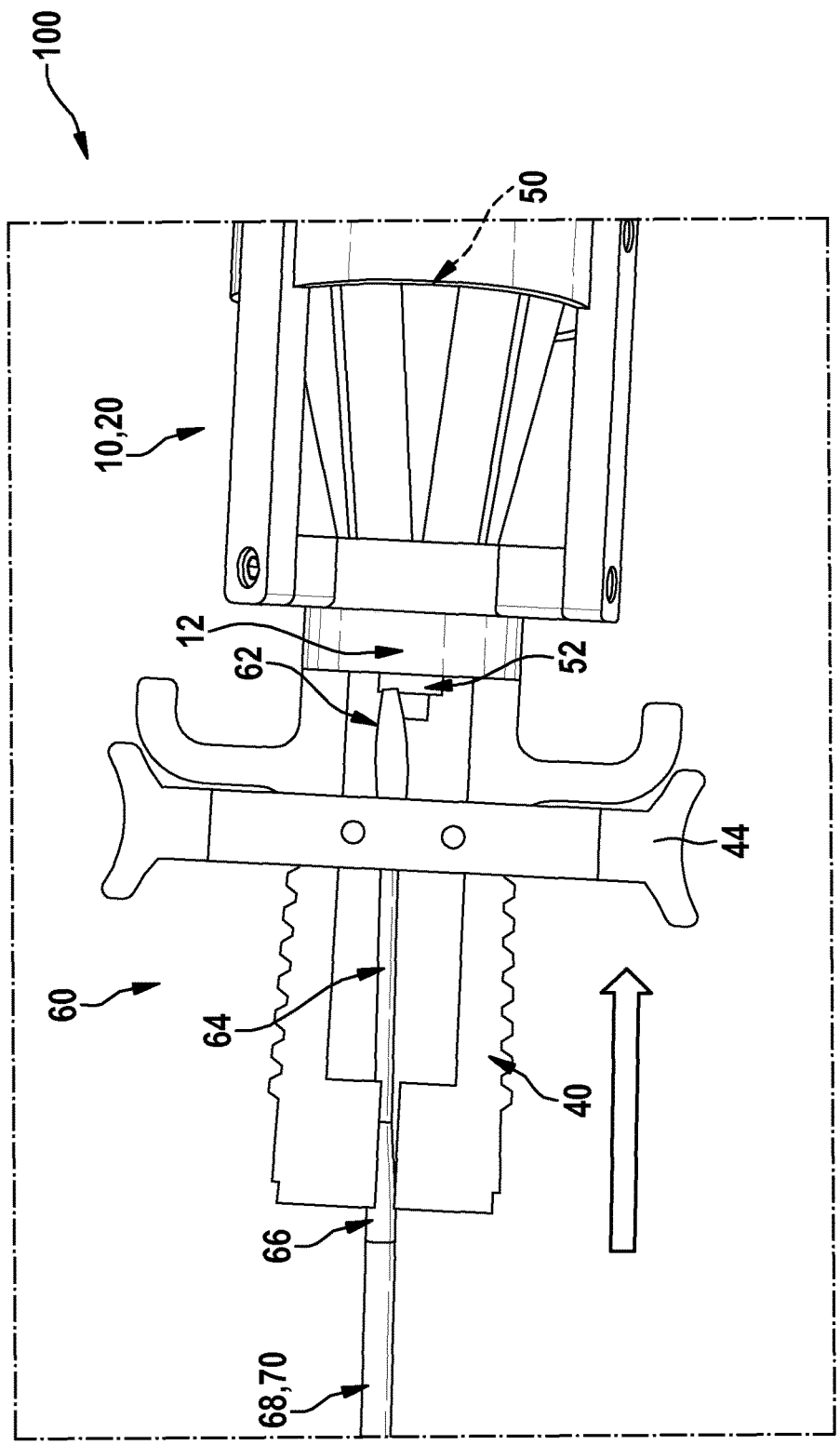
FIG. 7a a first method step in a saline bath where a catheter tip is introduced into a crimping tool which is preloaded with a prosthetic device with tangs of the prosthetic device protruding from a first member.

In FIG. 7a a first method step is shown where a catheter tip portion 60 is introduced into the crimping tool 100 which is preloaded with a prosthetic device with tangs 52 of the prosthetic device protruding from a first member 10. The catheter tip portion 60 has a tip 62, a loading area 64 where the prosthetic device shall be arranged in a collapsed state, attachment devices such as hooks 66 for locking the prosthetic device to the loading area 64 and a coupling potion 68 covered with a sheath 70. The sheath 70 is intended to cover the prosthetic device when arranged on the loading area 64 of the catheter tip portion 60.

Figure 7B:
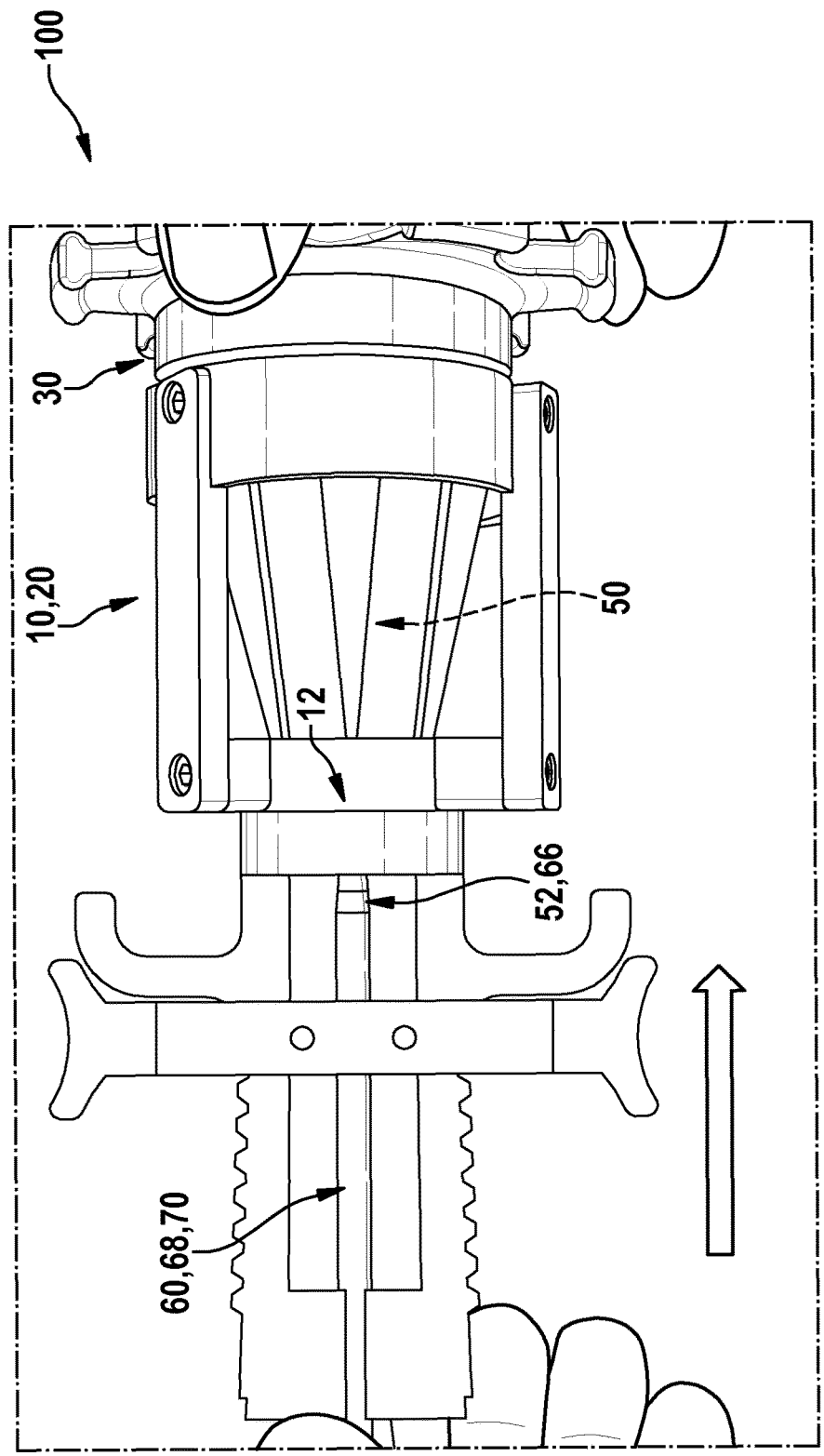
FIG. 7b a further method step where tangs of the prosthetic device are attached to the catheter tip for loading the prosthetic device to the loading area.

FIG. 7b shows a further method step where the tangs 52 of the prosthetic device are attached via hooks 66 to the catheter tip portion 60 for loading the prosthetic device to the loading area 64. The catheter tip portion 60 is inserted between the two legs 42 of the gripper element 40 and moved towards the second open end 12 of the first member 10, the movement being indicated by a bold arrow pointing towards the second end 12. The loading area 64 is now inside the first and second members 10, 20 and inside the prosthetic device 50 by help e.g. of a rod-like centre piece 35 as shown in FIG. 5.

Figure 7C:
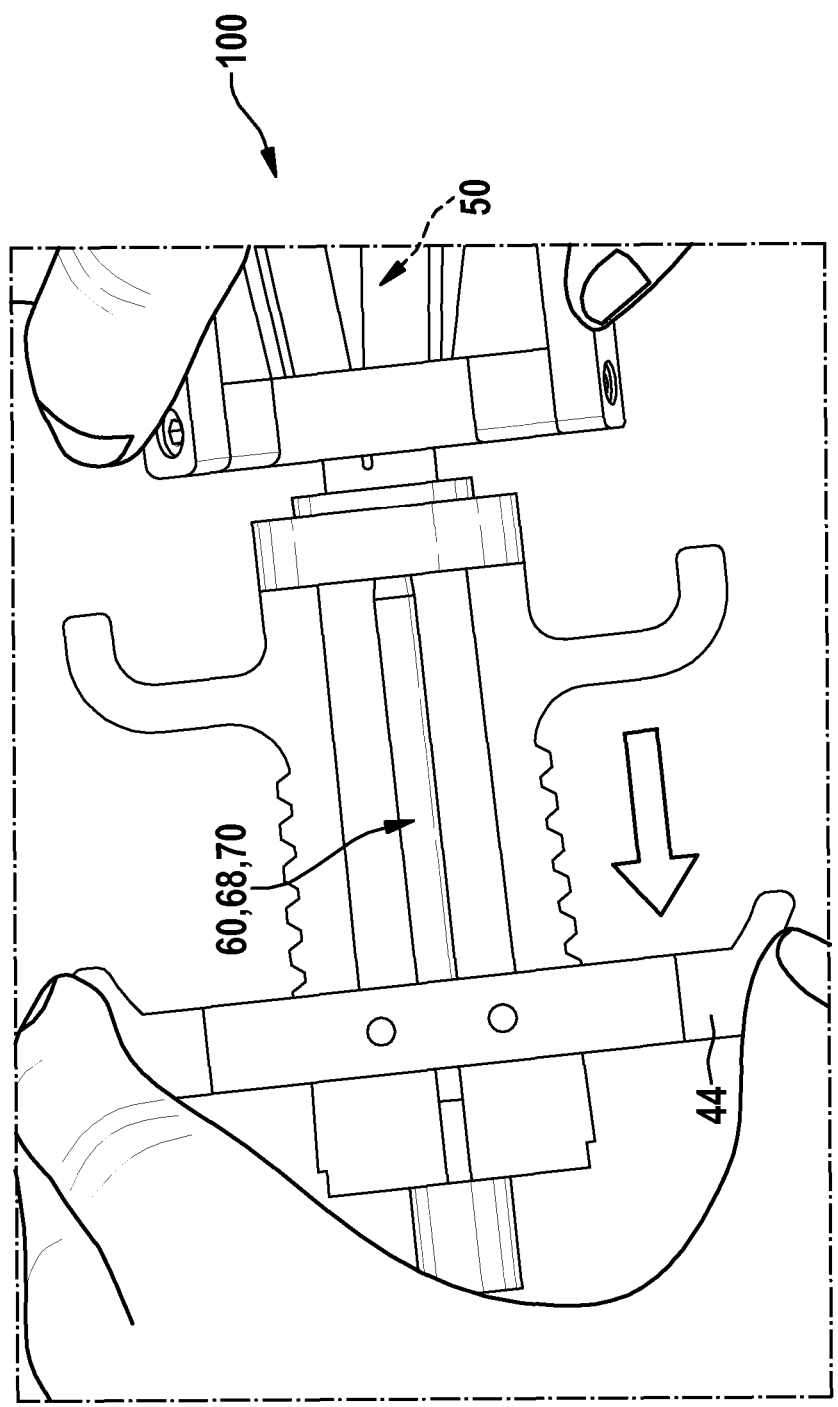
FIG. 7c a further method step where the catheter tip is locked in axial position.

FIG. 7c depicts a further method step where the catheter tip portion 60 is locked in axial position by moving the slider 44 away from the second end 12 of the first member 10 thus fixing the two legs 44 of the gripper element 40. The movement is indicated by a bold arrow pointing away from the second end 12 of the first member 10. The catheter tip portion 60 is now safely clamped between the two legs 42.

Figure 7D:
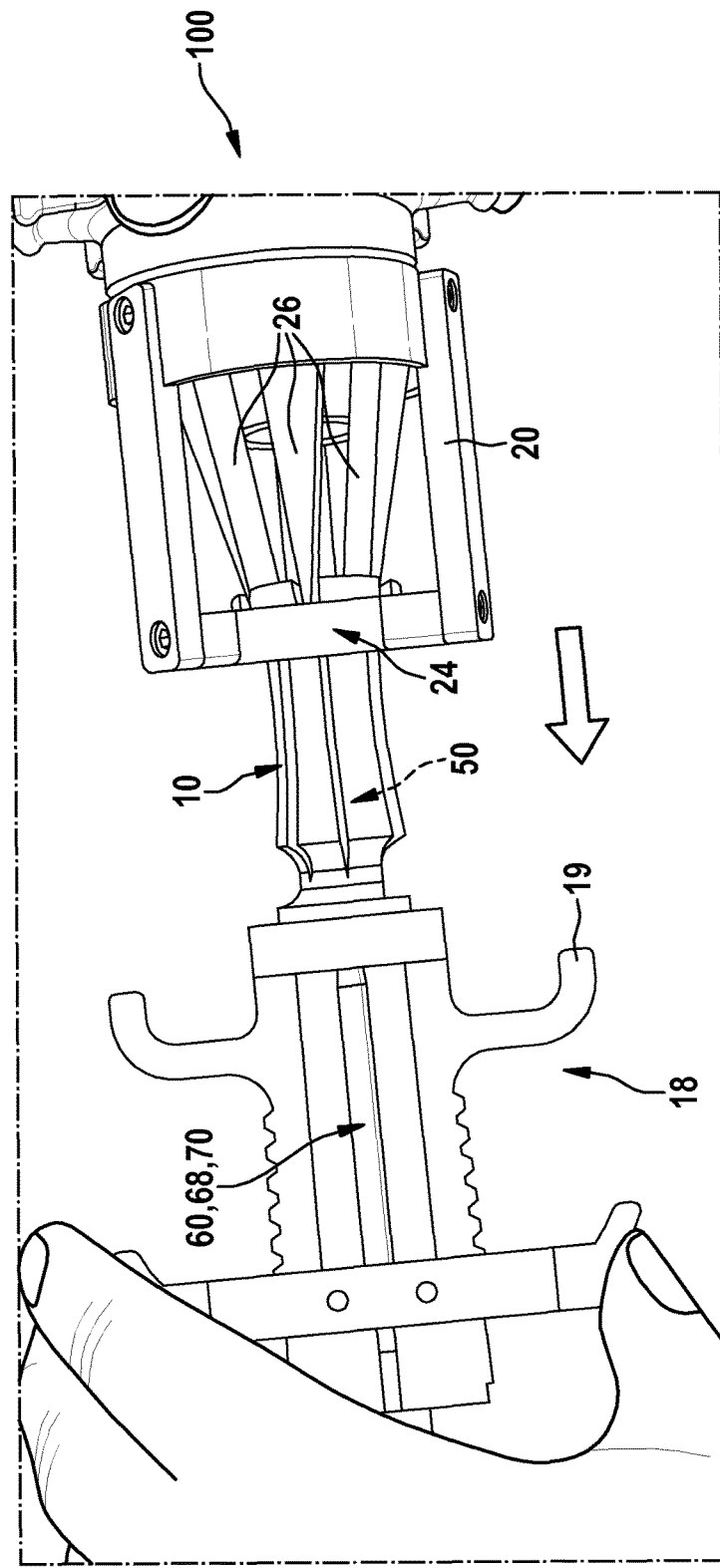
FIG. 7d a further method step where the first member is pulled through an engagement portion of a second member thus collapsing a first control surface and the prosthetic device on the loading area simultaneously.

FIG. 7d illustrates a further method step where the first member 10 is pulled via the activator element 18 through an engagement portion 24 of the second member 20 which results in collapsing a first control surface of the first member 10, and the prosthetic device 50 on the loading area 64 simultaneously. It can be seen that the shell portions 15 of the first members 10 which had been part of a conical shell before form now a predominantly cylindrical shell when pulled through the annular engagement portion 24. Rigid shell portions 25 of the second member 20 still are arranged in the conical shell. When the first member 10 is pushed back into the second member 20 these rigid shell portions 25 help the shell portions 14 of the first member 10 to spread to the frustoconical form.

Figure 7E:
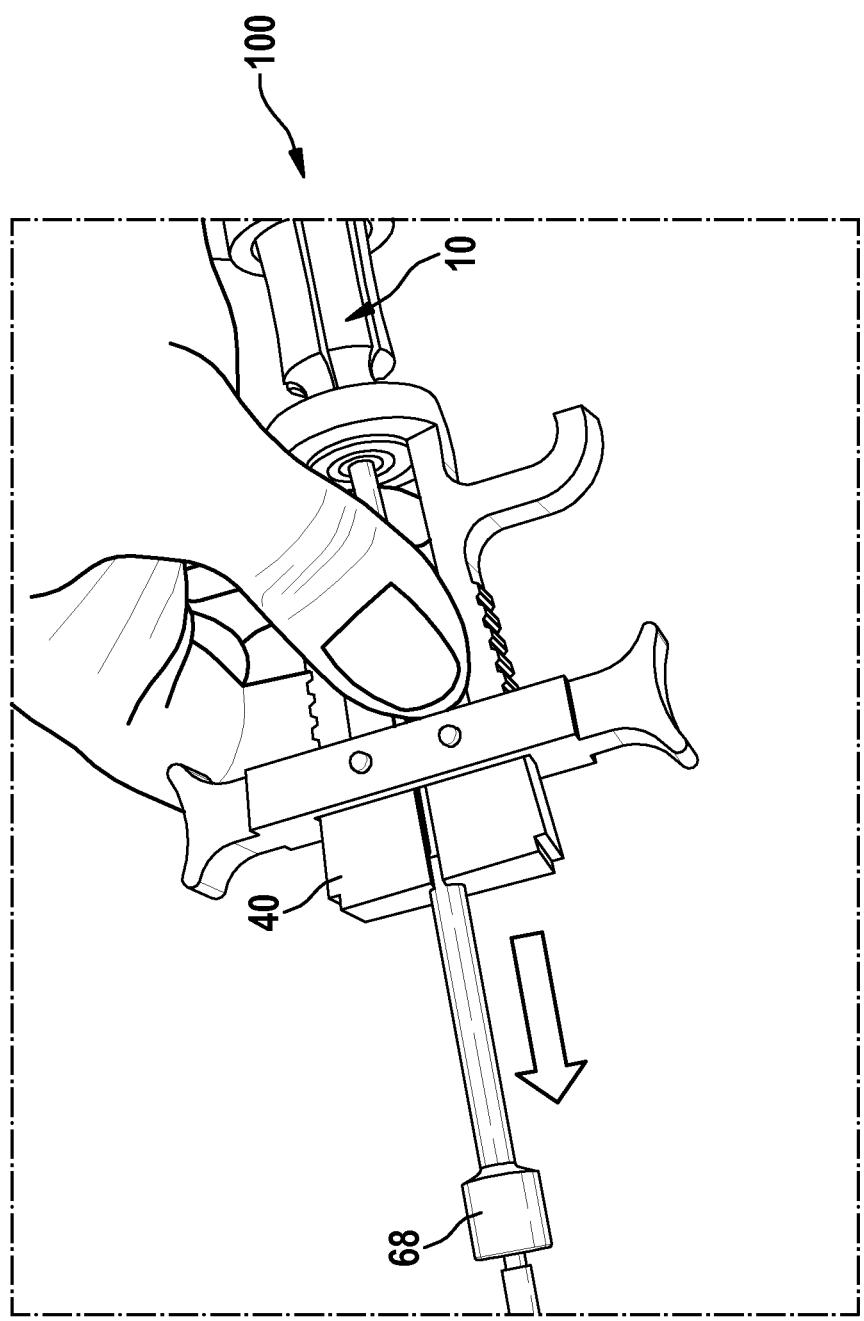
FIG. 7e a further method step where an outer sheath premounted on the catheter tip portion is moved over the loading area covered with the collapsed prosthetic device.

FIG. 7e shows a further method step where the outer sheath 70 premounted on the catheter tip portion 60 is moved over the loading area 64 about which is now arranged the collapsed prosthetic device 50. The sheath 70 can be held in place while the catheter tip portion 60 is pulled out of the crimping tool 100 which automatically moves the sheath over the loading area 64 covered by the prosthetic device 50. The crimping tool 100 can be used in gaseous as well as liquid atmosphere for crimping and collapsing the prosthetic device 50 and mounting the prosthetic device 50 to a catheter tip portion 60.

Figure 7F:
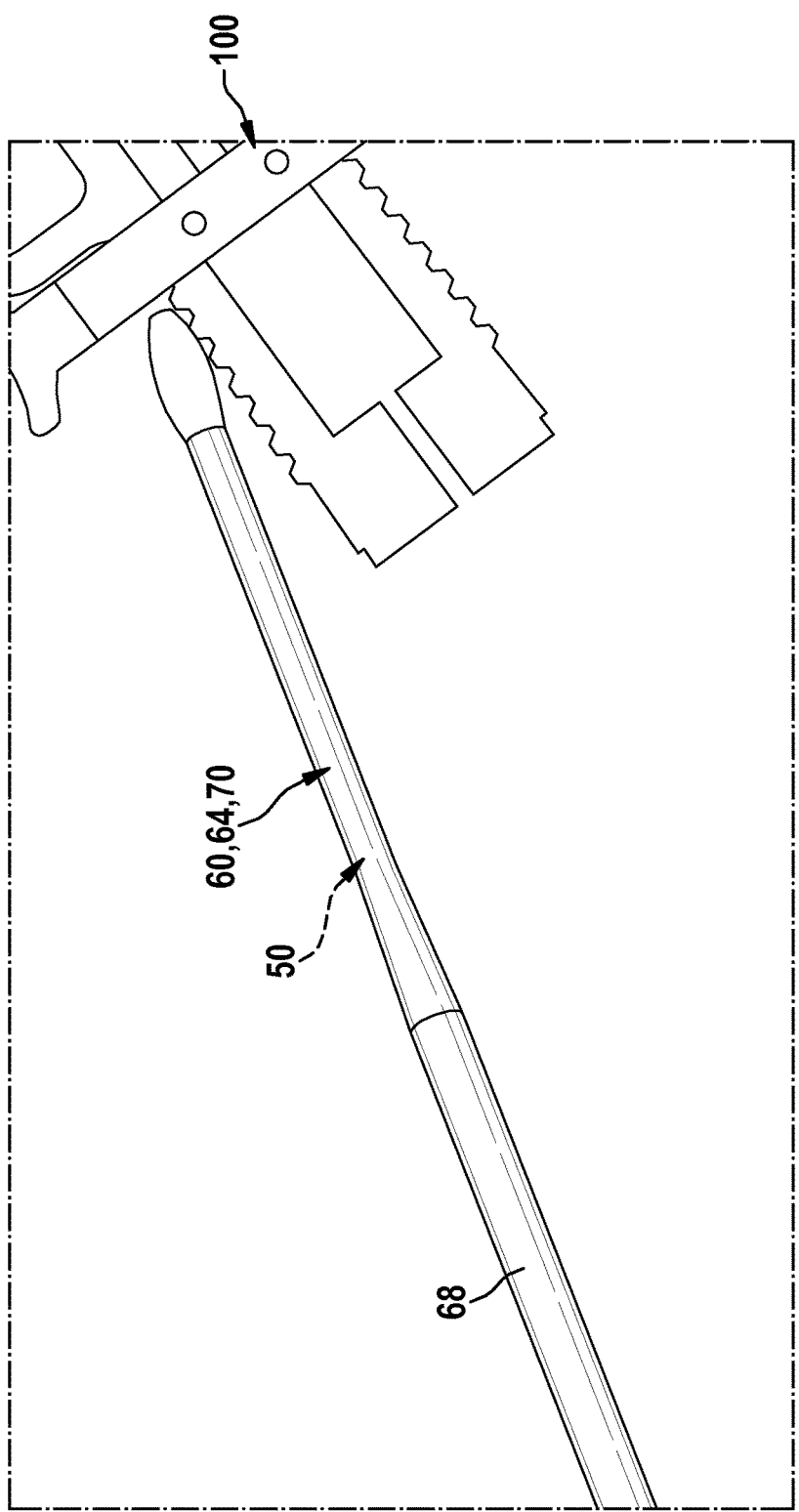
FIG. 7f the catheter tip portion having the collapsed prosthetic device arranged on its loading area covered with the outer sheath.

In FIG. 7f the catheter tip portion 60 having the collapsed prosthetic device 50 arranged on its loading area 64 covered with the outer sheath 70 is shown completely removed from the crimping tool 100. The catheter tip portion 60 can now be connected to a distal end of a delivery catheter and used for delivering the prosthetic device 50 to its intended location.

What is claimed is:

1. A crimping tool (100) for reducing an external dimension of a compressible prosthetic device (50) in a form of a heart valve, the crimping tool (100) comprising:
   a first member (10) comprising a longitudinal axis (L), a first control surface (15) collapsible between a first state and a second state, a first open end (11) configured for introducing a compressible prosthetic device (50) when in the first state, a second open end (12) configured for protrusion of prosthetic device (50) after introduction, and an actuator portion (18) for moving the first member longitudinally:
   a second member (20) comprising a first open end (21) and an opposing second open end (22), wherein the second open end (22) comprises an engagement portion (24) configured as a ring (24) with an opening (28) that interacts with the first member (10) as the first member (10) moves longitudinally to cause the first control surface (15) to move from the first state to the second state: and
   a third member (30) releasably connectable to the first end (21) of the second member (20), wherein the third member (30) has an annular collar configured for receiving a portion of the prosthetic device (50) during the introduction.

2. The crimping tool according to claim 1, wherein the first member (10) is configured as a collet having a receiving sleeve comprising a multitude of shell portions (14) separated by cuts predominantly parallel to the longitudinal axis (L), the multitude of shell portions (14) forming a splayed shell (13) in the first state of the first member (10), the multitude of shell portions (15) being attached to a ring (16).

3. The crimping tool according to claim 1, wherein the second member (20) is a cage structure configured to enclose the first member (10) when the first member (10) is in the first state.

4. The crimping tool according to claim 1, wherein the third member (30) comprises a screw thread (37) for connecting to the second member (20).

5. A method for crimping a prosthetic device in a form of a heart valve, the method comprising:
   providing a crimping tool (100) comprising:
   a first member (10) comprising a longitudinal axis (L), a first control surface (15) collapsible between a first state and a second state, a first open end (11) configured for introducing a compressible prosthetic device (50) when in the first state, a second open end (12) configured for protrusion of the prosthetic device (50) after introduction, and an actuator portion (18) for moving the first member longitudinally; a second member (20) comprising a first open end (21) and an opposing second open end (22), wherein the second open end (22) comprises an engagement portion (24) configured as a ring (24) with an opening (28) that interacts with the first member (10) as the first member (10) moves longitudinally to cause the first control surface (15) to move from the first state to the second state; and a third member (30) releasably connectable to the first end (21) of the second member (20), wherein the third member (30) has an annular collar for a portion of the prosthetic device (50);
   introducing a compressible heart valve into the first member (10) using the third member (30);
   engaging the second member (20) with the first member (10) using the engagement portion (24); and
   collapsing the first control surface (15) from the first state to the second state by passing the first member (10) through the engagement portion (24) longitudinally (L) thereby compressing the heart valve.

* * * * *